US011224394B2

(12) United States Patent
Schaefer et al.

(10) Patent No.: US 11,224,394 B2
(45) Date of Patent: Jan. 18, 2022

(54) SIGNALING OF AN AORTIC VALVE STATE

(71) Applicant: KONINKLIJKE PHILIPS N.V., Eindhoven (NL)

(72) Inventors: Dirk Schaefer, Hamburg (DE); Cherif Sahyoun, Eindhoven (NL); Eberhard Sebastian Hansis, Hamburg (DE); Christian Haase, Eindhoven (NL); Tobias Klinder, Uelzen (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 833 days.

(21) Appl. No.: 15/770,541

(22) PCT Filed: Oct. 27, 2016

(86) PCT No.: PCT/EP2016/075992
§ 371 (c)(1),
(2) Date: Apr. 24, 2018

(87) PCT Pub. No.: WO2017/072262
PCT Pub. Date: May 4, 2017

(65) Prior Publication Data
US 2019/0059839 A1 Feb. 28, 2019

(30) Foreign Application Priority Data
Oct. 28, 2015 (EP) .................................... 15191832

(51) Int. Cl.
*A61B 6/00* (2006.01)
*A61B 6/12* (2006.01)
(Continued)

(52) U.S. Cl.
CPC .............. *A61B 6/503* (2013.01); *A61B 5/339* (2021.01); *A61B 5/743* (2013.01); *A61B 6/12* (2013.01);
(Continued)

(58) Field of Classification Search
CPC ......... A61B 5/021; A61B 5/339; A61B 5/349; A61B 5/4836; A61B 5/743; A61B 6/12;
(Continued)

(56) References Cited

U.S. PATENT DOCUMENTS

2004/0249259 A1    12/2004  Heimdal
2007/0238979 A1*   10/2007  Huynh ................... A61B 5/103
                                                        600/420
(Continued)

FOREIGN PATENT DOCUMENTS

EP     1304074 A2     4/2003
EP     2896425 A1     7/2015
WO     2012095788 A1  7/2012

OTHER PUBLICATIONS

Kasel, Albert M. et al. "Anatomic Guided Crossing of a Stenotic Aortic Valve Under Fluoroscopy: Right Cusp Rule, Part III", JACC: Cardiovascular Interventions, vol. 8, No. 1, 2015.

*Primary Examiner* — Christopher L Cook

(57) ABSTRACT

The invention relates to an apparatus configured to display an aortic valve image and an indicator when the aortic valve is in its open-state and/or when the valve is in its closed-state. The indicator is supposed to be in an overlay to the image of the aortic valve, such that a physician can see on the same display image the information needed to advance a guide wire or catheter through the aortic valve of a heart. This may prevent damaging ensures not to damage the aortic valve. The physician receives the relevant information, when the aortic valve is in its open-state and thus being in a state to be passed by the catheter. The information, whether (Continued)

the aortic valve is in its open-state or in its closed-state, corresponds to the systolic phase and the distal phase of the heart, respectively. The information, when the heart is in its systolic phase and when it is in the diastolic phase may be extracted from an ECG measurement. From the detection of these cardiac phases, the closed-state of the valve and/or the open-state of the valve can be estimated using general knowledge about flood flow during the cardiac cycle.

14 Claims, 8 Drawing Sheets

(51) Int. Cl.
*A61B 5/00* (2006.01)
*A61B 5/339* (2021.01)
*A61B 8/08* (2006.01)
*A61B 5/021* (2006.01)
*A61B 8/00* (2006.01)
*A61B 5/349* (2021.01)

(52) U.S. Cl.
CPC ............ *A61B 6/4441* (2013.01); *A61B 6/463* (2013.01); *A61B 6/467* (2013.01); *A61B 6/5217* (2013.01); *A61B 5/021* (2013.01); *A61B 5/349* (2021.01); *A61B 8/085* (2013.01); *A61B 8/0841* (2013.01); *A61B 8/0883* (2013.01); *A61B 8/463* (2013.01)

(58) Field of Classification Search
CPC ........ A61B 6/4441; A61B 6/463; A61B 6/467; A61B 6/503; A61B 6/5217; A61B 8/0841; A61B 8/085; A61B 8/0883; A61B 8/463
See application file for complete search history.

(56) References Cited

U.S. PATENT DOCUMENTS

| | | |
|---|---|---|
| 2009/0281424 A1 | 11/2009 | Friedman |
| 2010/0161023 A1 | 6/2010 | Cohen |
| 2011/0160848 A1 | 6/2011 | Haase |
| 2013/0057569 A1 | 3/2013 | Liao |
| 2013/0108141 A1* | 5/2013 | Yamagata ............. G06T 7/0012 382/134 |
| 2013/0289391 A1 | 10/2013 | Levy |
| 2014/0294152 A1 | 10/2014 | Florent |
| 2016/0158006 A1* | 6/2016 | Sandhu ............. A61M 25/0108 604/529 |
| 2018/0228955 A1* | 8/2018 | Granegger ............ A61M 60/50 |

* cited by examiner

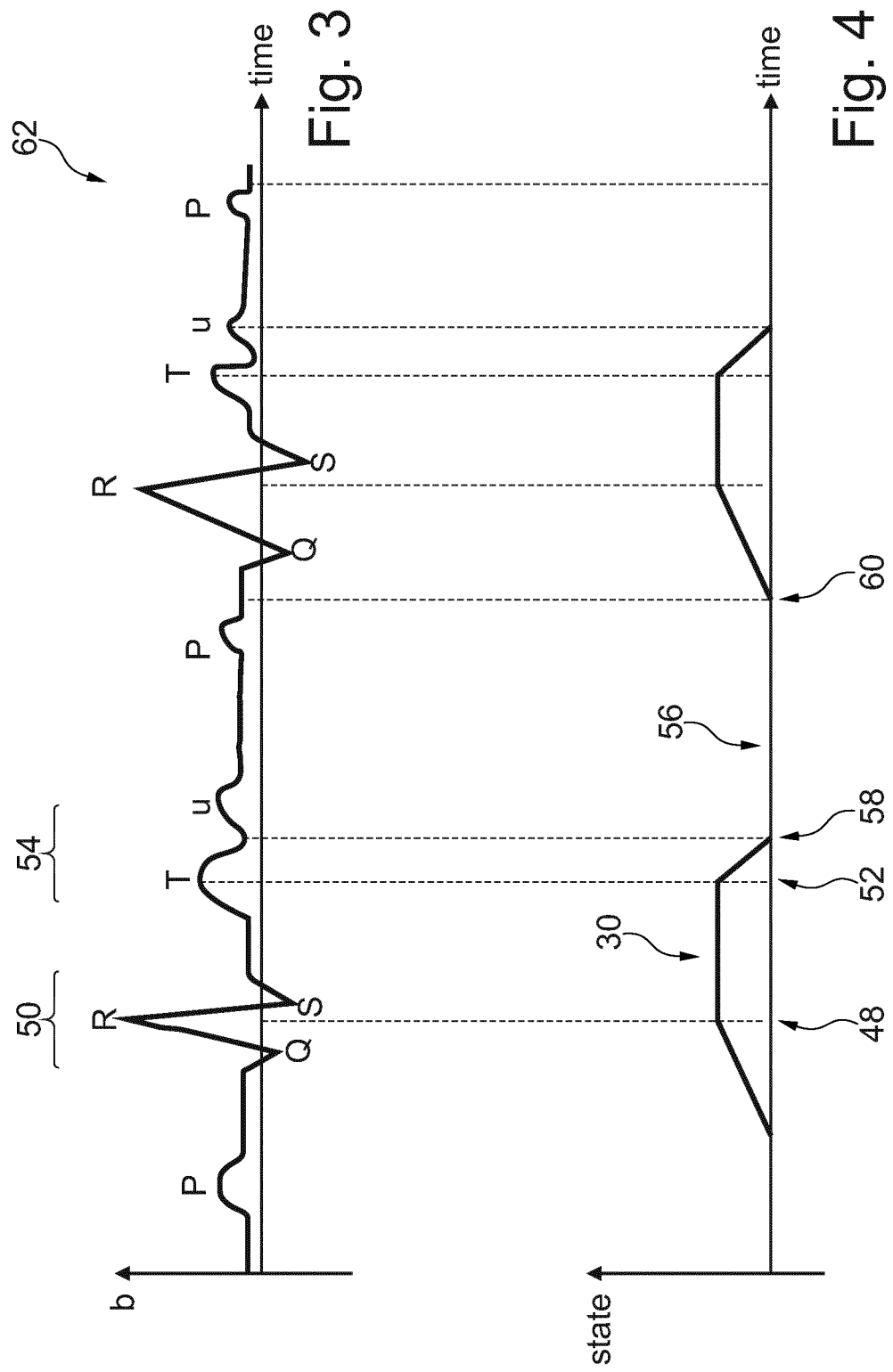

SIGNALING OF AN AORTIC VALVE STATE

CROSS-REFERENCE TO PRIOR APPLICATIONS

This application is the U.S. National Phase application under 35 U.S.C. § 371 of International Application No. PCT/EP2016/075992, filed on Oct. 27, 2016, which claims the benefit of European Patent Application No. 15191832.3, filed on Oct. 28, 2015. These applications are hereby incorporated by reference herein.

FIELD OF THE INVENTION

The present invention relates to the signaling of an aortic valve state, and in particular relates to an apparatus for signaling a state of an aortic valve, a system for signaling a state of an aortic valve, a method for signaling a state of an aortic valve, a computer program element and a computer-readable medium.

BACKGROUND OF THE INVENTION

The human heart comprises four valves and four chambers. The valves of the heart are located at the exit each of the four chambers of the heart. The valves are: the aortic valve, the pulmonary valve, the mitral valve, and the tricuspid valve. Each of the valves comprises flaps of tissue, or leaflets. The leaflets open and close as the heart pumps.

Defective heart valves may be either repaired or replaced. For repairing or replacing a defective valve, a catheter may be inserted into an artery or vein, usually in the leg. Usually, under X-ray and/or fluoroscopic visualization, the catheter is advanced into the heart and positioned at a site of the defective valve.

However, in order to position the catheter at the site of the defective valve, the catheter has to cross the defective valve first. The crossing of the defective valve in an early stage of the intervention is still considered challenging and is a time consuming task, which may take several minutes or even longer.

US 2013/0289391 A1 relates to a system and a method using forward looking imaging techniques for valve therapies. The system comprises a guide wire for guiding a catheter, wherein the guide wire comprises at its distal portion an imaging device containing a forward looking ultrasonic sensor. The ultrasonic sensor creates a field of view, which includes, in case the distal tip of the guide wire is close to the defective valve, at least a substantial portion of the defective valve. The ultrasonic beam can provide an image, which may be used to assist a positioning of the distal tip of the guide wire for a proper valve crossing.

US 2011/0160848 A1 relates to a method for crossing a heart valve. The method relates to the application of a guide wire, which comprises at its distal tip a diagnostic sensor, which may be configured to sense a velocity, a temperature and/or a pressure of the surrounding area. It is expected that the distal tip of the guide wire starts to vibrate or to "dance" when the distal tip is positioned within a blood jet at the outlet of a heart valve. This information may be used to indicate when the distal tip is properly positioned within the blood jet. Once the distal tip is positioned within the blood jet correctly, an increase of the vibration may be detected. Accordingly, the physician handling the guide wire may be able to synchronize an insertion of the guide wire into a left ventricle of an aortic valve with the systole phase of the heart. This reduces a risk of damage to the leaflets from crossing or insertion attempts during a diastole phase.

A guide wire having at its distal tip a sensor, in particular an ultrasonic sensor or a velocity sensor, may increase the size of the guide wire, at least at its distal tip. However, in order to be inserted into an artery or vein, a guide wire may have a size, that is as small as possible.

SUMMARY OF THE INVENTION

There may be a need to provide an improved support to a physician performing an aortic valve intervention. More in particular, there may be a need for an enhanced visualization of an aortic valve, which is supposed to be passed by a catheter.

The object of the invention is solved by the subject-matter of the independent claims, wherein further embodiments are incorporated in the dependent claims.

It should be noted that the following described aspects of the invention apply also for the apparatus, the system, the method, the computer program element and the computer-readable medium.

According to a first aspect of the invention, an apparatus for supporting an aortic valve intervention, comprising an input interface and a processing unit. The input interface is configured to receive i) an image-data signal g representing an X-ray image of an aortic valve of a heart and ii) a time variant, body-surface signal b indicating a beat of the heart. The processing unit is configured to determine an open-state of the aortic valve on the basis of the body-surface signal b, and to generate a display signal component for signaling the aortic valve as open during the determined open state of the aortic valve, and to generate a display signal representing a display image comprising the X-ray image and the display signal component.

Consequently, the display image advantageously shows, at least during the open-state of the aortic valve, a notation, which represents the aortic valve as open.

In an embodiment, the display image may show an overlay of at least a part of the aortic valve and a notation, which represents the aortic valve as open. The display image may support the physician in choosing the right time interval to advance a catheter to pass an aortic valve during its open-state.

As a further result, showing the display image comprising a notation about the open-state of the aortic valve may reduce a risk of a damage to the leaflets of the aortic valve.

Within the context of the present invention, the "open state" of the aortic valve is understood to refer to a state wherein the aortic valve is sufficiently open to allow the passage of an interventional device such as a guidewire or catheter. For example, the aortic valve is at its open state, if at least 70% of an aortic valve cross-section is of free passage to such device.

In the following, the term "catheter" may accordingly refer for any interventional device that needs to pass the aortic valve, including not only an actual catheter but also, for example, a guidewire.

In an example, the aortic valve image relates to an X-ray image of at least a part of the aortic valve of the heart. In an example, the image-data signal relates to an X-ray image-data signal. The image-data signal may be provided by an X-ray detector of an X-ray imaging unit.

In an example, the body-surface signal relates to a signal of a human body detected at its surface. The body-surface signal is preferably a non-tomographic signal. In a further example, the body-surface signal relates to a non-invasive body signal. The body-surface signal may be detected at a surface of the body, either directly or indirectly.

According to an exemplary embodiment, the body-surface signal is a blood pressure signal.

The blood pressure of a human increases and decreases periodically in correspondence to a beat of the heart. Consequently, a heartbeat may be determined from a blood pressure signal. Further, an open-state of an aortic valve may be determined on the basis of a heartbeat. Thus, the open-state of the aortic valve may also be determined on the basis of the blood pressure signal.

According to a further exemplary embodiment, the body-surface signal is an ECG-signal indicating an electric activity of the heart.

The ECG-signal relates to an Electrocardiography signal. The ECG-signal may be detected with electrodes placed on a human's body surface. The electrodes may detect electrical changes on the skin that arise from the heart muscle depolarizing during each heartbeat.

As an effect of the ECG-signal being the body-surface signal relates to the short time delay between the movement of the heart and the corresponding measured ECG-signal. Thus, the ECG-signal may be a real-time signal. Further, the states of the aortic valve, in particular the open-state of the aortic valve, can be determined precisely.

According to a further exemplary embodiment, the processing unit is configured to recognize a start of the open-state of the aortic valve based on a predefined start-open signal course of the body-surface signal, and wherein the processing unit is configured to recognize an end of the open-state of the aortic valve based on a predefined end-open signal course of the body-surface signal.

Thus, a start and an end of the open-state of the aortic valve may be recognized. The time from the start of the open-state to the end of the open-state may define an open-state time period of the aortic valve.

The heartbeat usually has a periodic character. Consequently, a surface signal, which allows determining states of the aortic valve, may also have periodic character. Thus, a part of the body-surface signal of each period may be characteristic for a start of the open-state. Another part of the body-surface signal at the same period may be characteristic for an end of the open-state of the aortic valve. Said parts of the body-surface signal may be defined by a signal course, which may be recognized at each period of the body-surface signal and thus being representative for the start of the open-state and the end of the open-state, respectively.

In an example, known signal detection steps may be performed in order to identify the start-open signal course and/or the end-open signal course at the body-surface signal. The detection may be a basis for recognizing the start of the open-state of the aortic valve and/or the end of the open-state of the aortic valve, respectively.

In an example, at least one characteristic point of the body-surface signal indicating a start of a systolic phase of the heart characterizes the start-open signal course.

In an example, at least one characteristic point of the body-surface signal indicating an end of a systolic phase of the heart characterizes the end-open signal course.

In an example, at least two of the characteristic points q, r, s, t indicate the systolic phase of the heart. Accordingly, the characteristic point q, in particular an end of a corresponding q-wave, may indicate a start of the systolic phase and/or start of the open-state of the aortic valve. The characteristic point t, in particular a peak of a corresponding t-wave, may indicate an end of the systolic phase and/or an end of the open-state of the aortic valve.

In an example, at least two characteristic points of the body-surface signal following each other indicating a start of a systolic phase of the heart characterizes the start-open signal course.

In a further example, at least two characteristic points of the body-surface signal following each indicating an end of the systolic phase of the heart characterize the end-open signal course.

In an example, the characteristic points q, r, s, t which relate to the qrs-complex, indicate the systolic phase of a heart. Accordingly, characteristic points q, r may indicate a start of the systolic phase and/or a start of the open-state of the aortic valve. The characteristic points s, t may indicate an end of the systolic phase and/or an end of the open-state of the aortic valve.

As a result, known detection techniques may be used for detecting the characteristic points q, r, s, t for each period of the heartbeat. On the basis of the detected characteristic points q, r, s, t, a start of the open-state of the aortic valve and/or an end of the open-state of the aortic valve may be determined.

As a further result, robust method steps can be used to determine the open-state of the aortic valve, since the determination of the open-state is based on signals and pre-processed results, which can be provided with known detection techniques. Thus, the determination of the open-state of the aortic valve is also robust.

According to a further exemplary embodiment, the processing unit is configured to determine a closed-state of the aortic valve on the basis of the body-surface signal, wherein the processing unit is configured to calculate, on the basis of the determined closed-state of the aortic valve, a further display signal component for signaling the aortic valve as closed during the closed-state of the aortic valve.

Within the context of the present invention, the "closed state" of the aortic valve is understood to refer to a state wherein the aortic valve is closed to the extent that the passage of an interventional device such as a guidewire or catheter is not practically feasible or even impossible. For example, the aortic valve is in its closed state, if at most 30% of an aortic valve cross-section is of free passage to such device.

As explained above, the processing unit is configured to provide a display signal comprising the display signal component or the further display signal component.

As a result, the display image may represent a notation to illustrate the aortic valve as closed during the closed-state of the aortic valve. Thus, a physician can directly see at the display image, whether the aortic valve is opened or closed. During the closed-state of the aortic valve, a proceeding of the catheter may be stopped, at least in case the catheter is positioned in front of the aortic valve.

It is understood that, without repeating here all the examples and explanations provided with reference to the open-state of the aortic valve, the determination of the closed-state of the aortic valve on the basis of the body-surface signal may be performed analogous to the determination of the open-state of the aortic valve on the basis of the body-surface signal.

According to a further exemplary embodiment, the processing unit is configured to recognize a start of the closed state of the aortic valve based on a predefined start-close signal course of the body-surface signal, wherein the processing unit is configured to recognize an end of the closed-state of the aortic valve based on a predefined end-close signal course of the body-surface signal.

In an example, at least one characteristic point of the body-surface signal indicating a start of a diastolic phase of the heart characterizes the start-close signal course.

In an example, at least one characteristic point of the body-surface signal indicating an end of a diastolic phase of the heart characterizes the end-close signal course.

In an example, at least two of the characteristic points t, u, p, q indicate the diastolic phase of the heart. Accordingly, the characteristic point t, in particular an end of a corresponding t-wave, may indicate a start of the diastolic phase and/or a start of the closed-state of the aortic valve. One of the characteristic points p, q, r, in particular a corresponding wave-end of point p, may indicate an end of the diastolic phase and/or an end of the closed-state of the aortic valve.

In an example, at least two characteristic points of the body-surface signal following each other indicating a start of a diastolic phase of the heart characterize the start-close signal course.

In an example, at least two characteristic points of the body-surface signal following each other indicating an end of a diastolic phase of the heart characterize the end-close signal course.

In an example, the characteristic points t, u, p, q indicate the diastolic phase of the heart. Accordingly, the characteristic points t, u may indicate a start of the diastolic phase and/or start of the closed-state of the aortic valve. The characteristic points p, q may indicate an end of the diastolic phase and/or an end of the closed-state of the aortic valve.

According to a further exemplary embodiment, the processing unit is configured to calculate, on the basis of the ECG-signal, a fourth display signal component for displaying an ECG-signal image.

It is understood that, without repeating here the effect of a further display signal component, the display signal may comprise the ECG image. In an example, the display image comprises an ECG-signal image in overlay and/or adjacent to the aortic valve image.

In a further example, the ECG-signal image is at least partly transparent.

In a further example, the ECG-signal may be an ECG live signal. Consequently, a physician may receive from the display image the aortic valve image, the ECG-signal and a notation indicating whether the aortic valve is at its open-state. Further, the physician may also receive from the notation whether the aortic valve is at its closed-state.

As an effect, the display image may provide a compact overview about relevant information of the aortic valve, especially in case a catheter is supposed to be passed through the aortic valve.

According to a further exemplary embodiment, the processing unit is configured to calculate the display signal component such that the open-state of the aortic valve is marked at the ECG-signal image between the start of the open-state of the aortic valve and the end of the open-state of the aortic valve.

In an example, a marker having a rectangular form may be used to mark the open-state of the aortic valve in the ECG-signal image.

In an example, the marker may be at least partly transparent and/or may be arranged in overlay to the ECG-signal image.

According to a further exemplary embodiment, the processing unit is configured to calculate the display signal component, such that at least a part of the aortic valve image is highlighted with a first color between the start of the open-state of the aortic valve and the end of the open-state of the aortic valve.

Preferably, a shape of the highlighted part is indicative of an area covered by a movement of the aortic valve between the open state and the closed state.

Thus, advantageously, in moving the catheter towards the aortic valve, a physician may avoid the interventional device obstructing the closing valve, or interfering therewith. In other words, the physician may be assisted in optimally positioning the catheter prior to advancing it across the aortic valve. The extent of the valve movement may be calculated from the length of the aortic valve leaflets as it may be extracted for example from computed tomography image data.

According to a further exemplary embodiment, the processing unit is configured to calculate the further display image component, such that at least a part of the aortic valve image is highlighted with a second color between the start of the closed-state of the aortic valve and the end of the closed-state of the aortic valve.

In an example, the first color is different to the second color.

In an example, the first color is green and the second color is red.

In an example, the highlightings are each at least partly transparent.

According to a further exemplary embodiment, the processing unit is configured to recognize a tip-position of a tip of a catheter in the aortic valve image. The recognition may be image-based or may be based on position tracking of, for example, an electromagnetic transducer on the tip. The processing unit is further configured to recognize, a valve-position of the aortic valve in the aortic valve image, and to calculate a catheter-distance between the tip-position and the valve-position. The display signal components may be enabled to be a part of the display signal, in case the catheter-distance is smaller than a predefined minimum-distance, and disabled otherwise.

As an effect, the display image may comprise the information about a state of the aortic valve, in case the catheter is close to the aortic valve. Thus, the information about the state of the aortic valve is just displayed, when the information is needed. Consequently, the information provided at a respective display can be reduced. This may increase the concentration of a physician when using the apparatus.

According to a further exemplary embodiment, the apparatus may further comprise an acoustic output unit, wherein the processing unit is configured to calculate, on the basis of the determined open-state of the aortic valve, an acoustic signal for signaling the aortic valve as open during the open-state of the aortic valve, and wherein the acoustic output unit is configured to acoustically indicate the open-state of the aortic valve on the basis of the acoustic signal.

As an effect, a physician using the apparatus may acoustically hear, when the aortic valve is at its open-state and thus acoustically receiving an indication for a good time for proceeding the catheter.

As a further effect, a user, in particular the physician, may not need to look at the display in order to receive the information about the state of the aortic valve, in particular about the open-state of the aortic valve. Consequently, the physician may concentrate on other aspects for placing the catheter at the desired position.

According to a further exemplary embodiment, the apparatus comprises an output unit, wherein the processing unit is configured to calculate, on the basis of the determined open-state of the aortic valve, an output signal for signaling the aortic valve as open during the open-state of the aortic valve and wherein the output unit is configured to provide the output signal for further purposes.

As an effect, the output signal may be provided to a further unit of the apparatus or to a further device. At the further unit or the further device, the output signal may be provided to the attention of the user, in particular to a physician. This may be done optically, acoustically and/or haptically.

According to a further exemplary embodiment, the apparatus comprises a catheter and a signal connection, wherein the signal connection connects the output unit of the apparatus and the catheter, wherein the catheter provides a handle to operate the catheter, and wherein the catheter provides at or next to the handle a haptic unit, for instance comprising a vibration element, configured to haptically indicate the open-state of the aortic valve on the basis of the output signal.

As an effect, the user of the apparatus handling the catheter may haptically receive the information about the open-state of the aortic valve. Thus, the physician may not need to look at a display of the apparatus and thus being able to concentrate on other issues while processing the catheter through the aortic valve.

According to a second aspect of the present invention, a system for signaling a state of the aortic valve is provided, comprising: an apparatus according to any of the preceding examples of the apparatus, an X-ray imaging unit for acquiring the aortic valve image, a body-surface signal detection unit for providing the body-surface signal, and a display unit for displaying the display image.

According to a third aspect of the invention, a method for signaling a state of an aortic valve is provided, comprising the steps of receiving an image-data signal representing an X-ray image of an aortic valve of a heart, receiving a time variant, body-surface signal indicating a beat of the heart, determining an open-state of the aortic valve on the basis of the body-surface signal, generating a display signal component for signaling the aortic valve as open during the determined open state of the aortic valve, and generating a display signal representing a display image comprising the X-ray image and the display signal component.

According to a fourth aspect of the present invention, a computer program element is provided, which, when being executed by a processing unit, is adapted to carry out the method described above.

According to a fifth aspect of the present invention, a computer-readable medium having stored thereon a program element is provided, which, when being executed by a processing unit, is adapted to carry out the method described above.

According to a further aspect of the invention, it is proposed to display, additionally to an aortic valve image, in particular based on a motion compensated aortic valve model, an indicator when the valve is in the open-state and/or when the valve is in the closed-state. The indicator is supposed to be an overlay to the image of the aortic valve, such that the physician can see on the same display the information needed to advance a catheter through the aortic valve of a heart. This ensures not to damage the aortic valve. Instead, the physician receives the relevant information, when the aortic valve is in its open-state and thus, the catheter may be advanced without any damage of the aortic valve. The information, whether the aortic valve is in its open-state or in its closed-state, corresponds to the systolic phase and the distal phase of the heart, respectively. The information, when the heart is in its systolic phase and when it is in the diastolic phase may be extracted from an ECG measurement. From the detection of these cardiac phases, the closed-state of the valve and/or the open-state of the valve can be estimated using general knowledge about flood flow during the cardiac cycle.

The display image may provide a graphical guidance, wherein a green flag or a frame may be provided at the display image to indicate that the aortic valve is in its open-state.

Two-dimensional and/or three-dimensional tracking of the catheter may be integrated to enable additionally functionality. According to a preferred example, the graphical indication of the states of the aortic valve can be enabled and/or disabled depending on a distance between the catheter and the aortic valve. If the distance is too large, the indication is disabled. If the distance is smaller than a predefined threshold distance, the indication is enabled. Information of the two-dimensional or three-dimensional distance of the catheter to an aortic wall of the aortic valve and/or the aortic valve as such can be integrated in the display image in order to add a further indicator at the display image. Generally, if the catheter is positioned at the center with respect to the aortic valve, an easier crossing of the aortic valve is expected.

These and other aspects of the present invention will become apparent from and be elucidated with reference to the embodiments described hereinafter.

BRIEF DESCRIPTION OF THE DRAWINGS

Exemplary embodiments of the invention will be described in the with reference to the following drawings.

FIG. 3 schematically illustrates an ECG signal.

FIG. 4 schematically illustrates the states of an aortic valve.

DETAILED DESCRIPTION OF THE EMBODIMENTS

In the following, the invention is exemplarily described as being used in the context of an X-ray imaging system 24 for trans-catheter aortic valve implementation (TAVI). The invention can also be used in the context of other heart interventions and/or diagnostics.

In trans-catheter aortic valve implementation interventions, a critical point is the precise positioning of the implementable device. To achieve this position, for instance a supra-aortic angiography (preferably with contrast agent) can be performed in order to determine a good or optimal projection of the valve deployment. An image, preferably featuring good contrast, can be selected, stored, and/or subsequently used as a pre-implant reference image. The contrast injection can be achieved through a so-called pigtail catheter placed in the aortic root. In order to facilitate accurate positioning, road mapping and/or outlining methods can be used. This may consist in super-imposing to the live view (for example, fluoroscopy without contrast agent) an anatomic representation of the anatomy (for example, contours of the aortic route as extracted from a reference aortogram, an anatomy model derived from a 3D pre-interventional data, and/or a combination of both, or any other suitable representation). This anatomy representation can then be correctly registered with live images. The continuous registration process with live images is often referred to as tracking.

Exemplary embodiments of the invention will be described in the following with reference to the following drawings.

Figure 1:
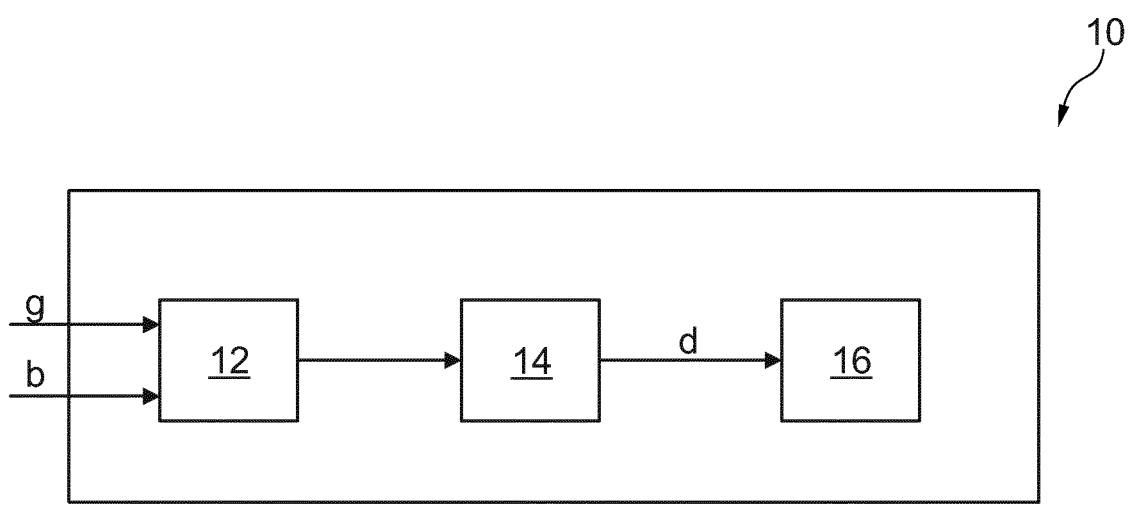
FIG. 1 schematically illustrates an example of the apparatus.

FIG. 1 schematically illustrates an apparatus 10 for signaling a state of an aortic valve. The apparatus 10 comprises an input interface 12, a processing unit 14, and a display unit 16. The input interface 12 is configured to receive an image-data signal g indicating an aortic valve X-ray image 20 of a heart. The input interface 12 is configured to receive a time variant, body-surface signal b indicating a beat of the heart. The processing unit 14 is configured to determine an open-state 30 of the aortic valve on the basis of the body-surface signal b. The processing unit 14 is configured to calculate, on the basis of the image-data signal g, a first display signal component for illustrating the aortic valve image 20 of the aortic valve. The processing unit 14 is configured to calculate, on the basis of the determined open-state 30 of the aortic valve, a second display signal component for signaling the aortic valve as open during the open-state 30 of the aortic valve. The processing unit 14 is configured to provide a display signal d comprising the display signal components. The display unit 16 is configured to display a display image 22 on the basis of the display signal d.

Figure 2:
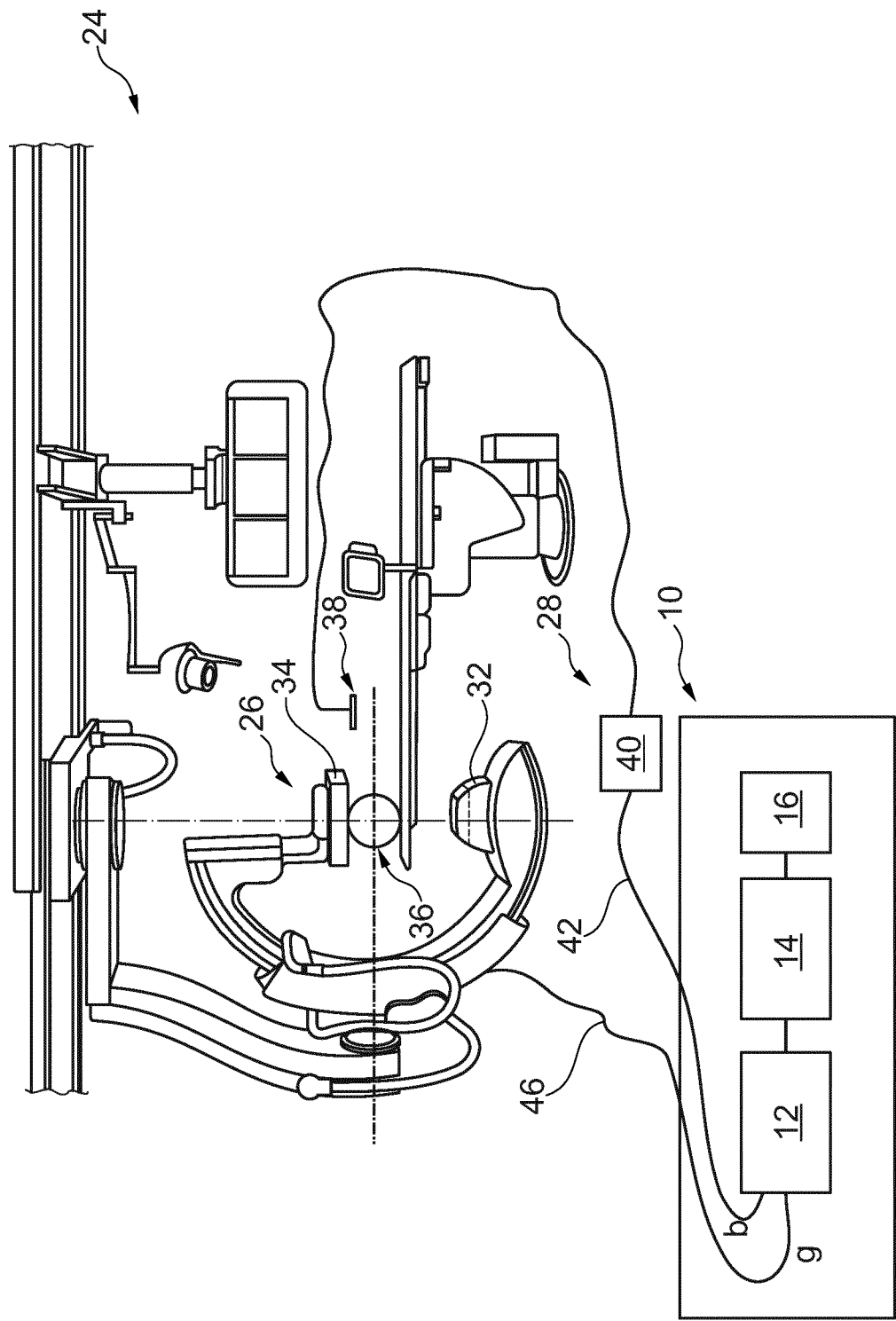
FIG. 2 schematically illustrates an X-ray imaging system.

FIG. 2 schematically shows a system 24 for signaling a state of an aortic valve. The system 24 comprises the apparatus 10, an X-ray imaging unit 26, and a body-surface signal detection unit 28. The X-ray imaging unit 26 is configured to acquire an X-ray image 20 of an aortic valve of a heart and to provide an image-data signal g indicating the aortic valve X-ray image 20. In particular, a sequence of live fluoroscopy X-ray images may be acquired to guide the advancing towards, and passing of, an aortic valve by a catheter or guidewire.

The body-surface signal detection unit 28 is configured to detect a body-surface signal b indicating a beat of the heart. The body-surface signal detection unit 28 is configured to provide a live, time variant, body-surface signal b indicating the beat of the heart.

It is to be understood that, without repeating all the following examples and explanations provided with reference to the system, the same examples and explanations hold in analogous manner for the apparatus. Thus, all provided features, examples and effects are also intended to be implemented by the apparatus as such. Examples, features and/or explanations described with respect to the apparatus are to be understood with regard to the system vice versa.

FIG. 1 shows an example of the apparatus 10.

Although FIG. 2 shows the apparatus 10 in the context of the system 24, the apparatus 10 can be a stand-alone apparatus 10 and can be provided separately. The system 10 may be an X-ray imaging system 24, in particular shown in FIG. 2 with reference to a C-arm system.

The system 24 may comprise an X-ray source 32 and an X-ray detector 34. The X-ray source 32 may be configured to radiate X-ray radiation towards the detector 34 radiating at least a part of a region of interest of a human body 38, in particular the respective aortic valve. In FIG. 2, a part of the human body is represented by a circle. The X-ray detector 34 may be configured to provide the image-data signal g, preferably as a live image-data signal g.

The body-surface detection unit of the system 24 may comprise a body-surface signal detector 38 and a pre-processing unit 40. In an example, the pre-processing unit 40 may be spaced apart of the apparatus 10, while being interconnected via a signal line 42.

The display signal d comprises at least the image-data signal g representing the aortic valve X-ray image 20 as a first display signal component and the display signal component for signaling the aortic valve as open during the open-state 30 of the aortic valve as a second display signal component. As a result, the display image 22 may be generated on the basis of the first and second signal components.

Figure 5:
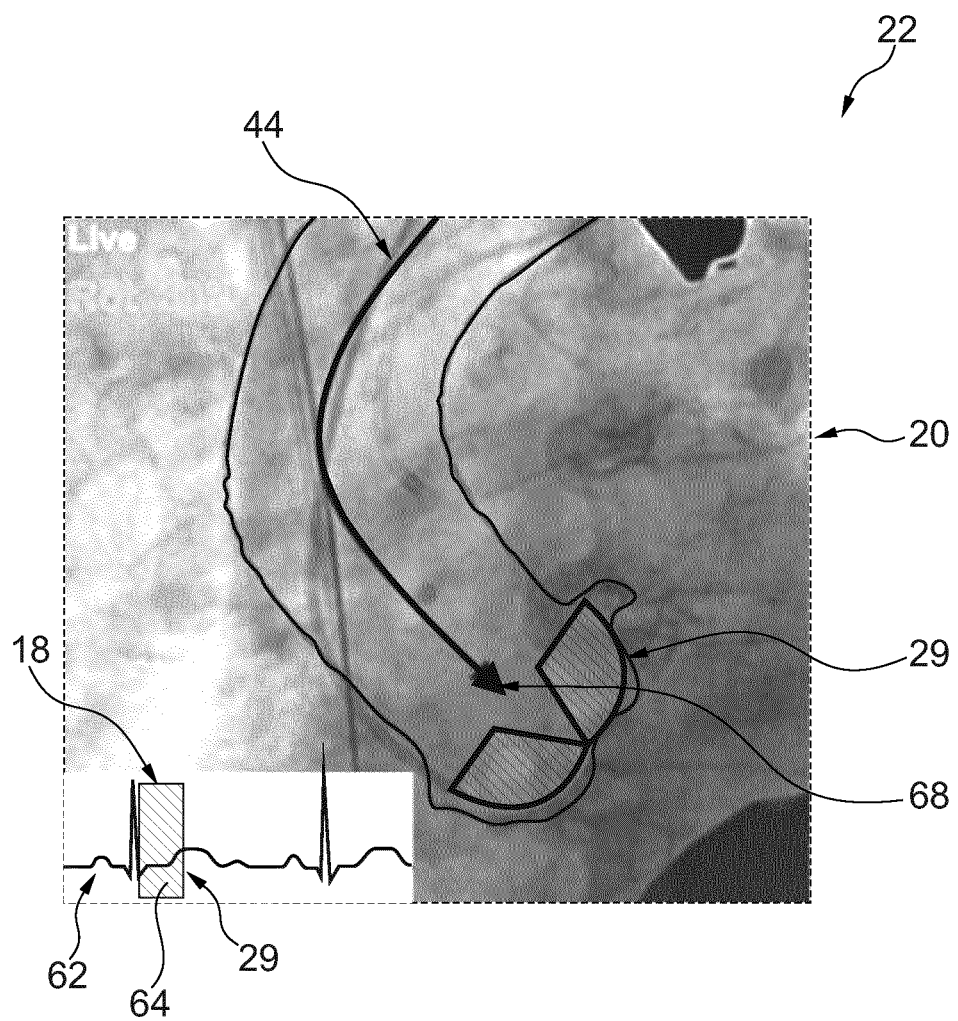
FIG. 5 shows an X-ray image with an overlay to indicate an open aortic valve of a heart.
Figure 6:
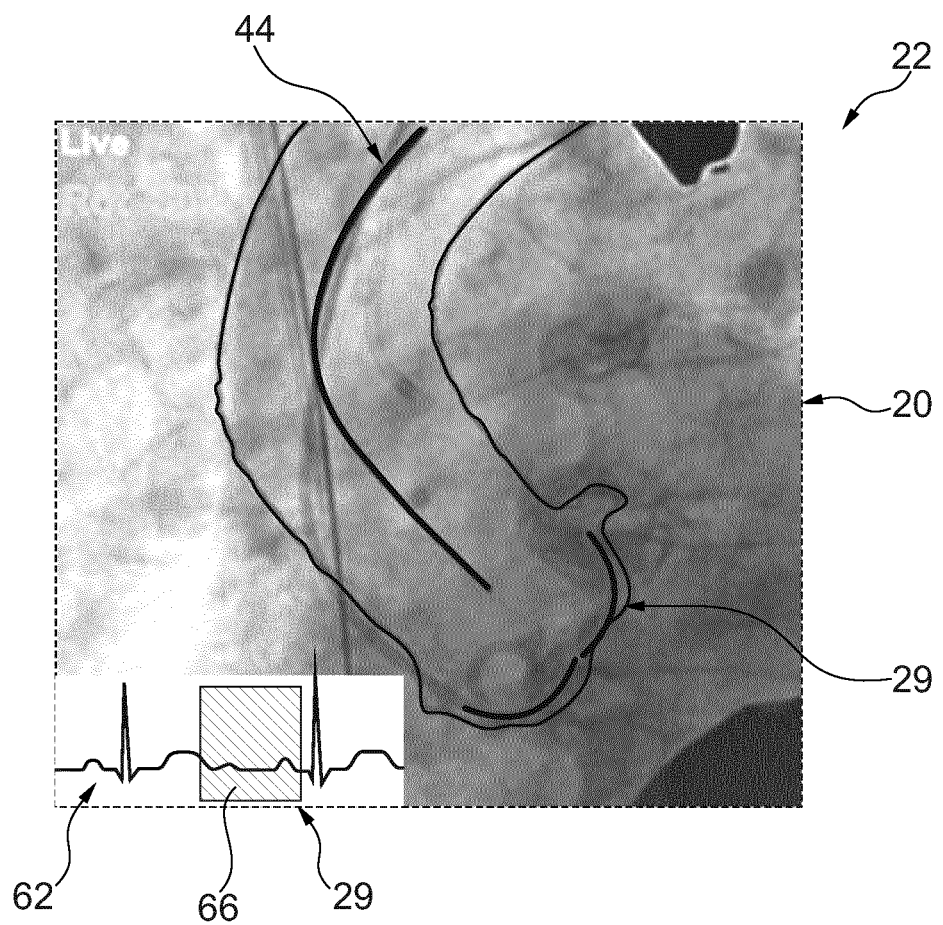
FIG. 6 shows an X-ray image with an overlay to indicate a closed aortic valve of the heart.

FIG. 5 and FIG. 6 show examples of display images 22, which comprise a notation 29 as the second display signal component to indicate the state of the aortic valve, and at least a part of the aortic valve image 20.

As a result, the display image 22 may show at least a part of the aortic valve and the notation 29 as an overlay thereto. An example of the display image is shown in FIG. 5 representing the aortic valve as open. The display image 22 may support the physician in choosing the right time interval to advance a catheter 44 to pass the aortic valve during its open-state 30.

In this preferred embodiment, the notation 29 is shaped so as to indicate an extent of the movement of the aortic valve leaflets when the valve changes from its open state to its closed state or vice versa.

The catheter 44 may by indicated at the aortic valve image 20 and/or the display image 22 by a linear marking as an overlay.

As a further result, showing the display image 22 comprising a notation 29 for instance indicating the open-state 30 of the aortic valve and the movement extent of the valve leaflets may support a physician in optimally position the catheter 44 in advancing towards the aortic valve prior to passing it and thereby reduce a risk of damaging the leaflets of the aortic valve.

In an example, the aortic valve image 20 relates to an X-ray image of at least a part of the aortic valve of the heart. The system 24 may be used to provide such an image. In an example, the image-data signal g relates to an X-ray image-data signal of the system 24. The image-data signal g may be provided by an X-ray detector 32 of the system 24.

In an example, the body-surface signal b relates to a signal of a human body detected at its skin. In a further example, the body-surface signal b relates to a non-invasive body signal. The body-surface signal b may be detected at the skin of the body, either directly or indirectly. For instance, the body-surface signal b may be detected with the detector 38 having direct contact with the skin of the human body 36. However, a detector 38 may be provided, which can be arranged at a distance or apart to the skin of the body 36, however, being able to detect a body-surface signal b of the human body 36 at its skin.

In an example, the image-data signal g may be time invariant. For example, the image-data signal g may relate to an X-ray image-data signal, which has been produced once and provided to the input interface 12 of the apparatus 10.

Thus, a signal line 46 may be provided between the detector 32 and the input interface 12 for transmitting the image-data signal g.

In a further example, the image-data signal g may be provided from a C-arm X-ray unit comprising the detector 32 to the input interface 12 via the signal line 46.

In an alternative example, the image-data signal g may be a time variant. Thus, the image-data signal g may indicate the aortic valve image in a time variant manner. Accordingly, the aortic valve image 20 may be a time variant image. The aortic valve image 20 may illustrate movements of the aortic valve corresponding to the image-data signal g.

In a further example, the image-data signal g and/or the body-surface signal b are provided by a server.

In an example, the image-data signal g and the body-surface signal b are synchronous, time variant signals. Further, the image-data signal g and the body-surface signal b may be synchronous, live, time variant signals.

The aortic valve of the heart is periodically opened and closed. In an example, the aortic valve is at its open-state, if at least 70% of an aortic valve cross-section is of free passage. In an example, the aortic valve is at is closed-state, if at most 30% of the aortic valve cross-section is of free passage. Between a closed-state and an open-state 30, the aortic valve may be at an intermediate-state. The states of the aortic valve may correlate to a beat of the heart and/or may be a function of the beat of the heart. The beat of the heart may be detected at the surface of a human, to which the heart belongs to. For instance, a blood pressure signal may be detected at the surface of the human. The blood pressure signal may be a function of the beat of the heart. Correspondingly, the states, and in particular the open-state 30, of the aortic valve may be a function of the blood pressure signal. Further, a body-surface signal may be a nerve signal, which can be detected at the surface of the human. The nerve signal may relate to the heart of the human. Thus, the nerve signal may indicate a beat of the heart. Correspondingly, a state of the aortic valve, in particular an open-state 30 of the aortic valve, may be a function of an electronic signal of a nerve of the human. Further signals, which can be detected at the surface of the human, may represent a signal, which may be used as an argument of a function to determine an open-state 30 of the aortic valve.

Body-surface signals b is usually easily to detect. Thus, providing information about the open-state 30 of the aortic valve may be easily provided by calculating the open-state 30 of the aortic valve on the basis of the body-surface signal b.

Further, the display signal d comprises the display signal components. Thus, the display image 22 displayed by the display unit 16 may show information about the aortic valve and about the open-state 30 of the aortic valve, at least in case the aortic valve is at its open-state 30.

As a result, the apparatus 10 provides a display image 22, which allows to easily receiving information about the aortic valve and a good time, when a catheter 44 may be advanced in order to pass the aortic valve.

According to an example, the body-surface signal b is a blood pressure signal.

The blood pressure of a human increases and decreases periodically in correspondence to a beat of the heart. Consequently, a heartbeat may be determined from a blood pressure signal. Further, an open-state 30 of an aortic valve may be determined on the basis of a heartbeat. Thus, the open-state 30 of the aortic valve may also be determined on the basis of the blood pressure signal.

In an example, the blood pressure signal as the body surface signal b may be detected via a tactile blood pressure sensor 38. Accordingly, a blood pressure signal provided by the blood pressure sensor is a non-invasive signal. Furthermore, the blood pressure signal is a non-tomographic signal. The blood pressure signal can be easily detected. Corresponding detection elements are known and provided in the state of the art.

In an example, the blood pressure signal may be detected via a surface image camera. An increase of the blood pressure may tighten a skin of a human. A decrease of the blood pressure may relax the skin. These changes of the skin can be detected via surface image camera. Consequently, a blood pressure signal can be determined on the basis of the signal provided by the surface image camera.

As an effect, non-invasive detection elements can be used to provide a body-surface signal b, and in particular a blood pressure signal. Such detection elements can be easily implemented and are of low cost. Furthermore, a complexity of a catheter can be limited, since no further detection elements have to be contained by the catheter 44 in order to provide a timing for the advancing of the catheter 44 when being in front of the aortic valve.

According to a further example, the body-surface signal b is an ECG-signal indicating an electric activity of the heart.

The ECG-signal relates to an Electrocardiography signal. The ECG-signal may be detected with electrodes placed on a human's body surface. The electrodes may detect electrical changes on the skin that arise from the heart muscle depolarizing during each heartbeat. Thus, the ECG-signal may be detected via an ECG detection unit, in particular comprising an ECG sensor.

In an example, the ECG-signal may be a live ECG-signal.

As an effect of the ECG-signal being the body-surface signal b relates to the short time delay between the movement and/or the beat of the heart and the correspondingly measured ECG-signal. The ECG-signal may be a real time signal. Thus, the states of the aortic valve, in particular the open-state 30 of the aortic valve, can be determined precisely. Furthermore, the states of the aortic valve, in particular the open-state 30 of the aortic valve, may be determined in real time.

In FIG. 3, an example of a periodic ECG-signal of a human body 36 as the body-surface signal b is shown. The characteristic points q, r, s, t, preferably relating to the qrs-complex, indicate the systolic phase of a heart of the human body 36.

According to a further example, the processing unit 14 is configured to recognize a start 48 of the open-state 30 of the aortic valve based on a predefined start-open signal course 50 of the body-surface signal b, wherein the processing unit 14 is configured to recognize an end 52 of the open-state 30 of the aortic valve based on a predefined end-open signal course 54 of the body-surface signal b.

Thus, a start 48 and an end 52 of the open-state 30 of the aortic valve may be recognized from the ECG-signal. The time from the start 48 of the open-state 30 to the end 52 of the open-state 30 may define an open-state time period of the aortic valve.

The heartbeat usually has a periodic character. Consequently, a body-surface signal b, which allows determining states of the aortic valve, may also have periodic character. Thus, a part of the body-surface signal b at each period may be characteristic for the start 48 of the open-state. Another part of the body-surface signal b at the same period may be characteristic for the end 52 of the open-state 30 of the aortic valve. Said parts of the body-surface signal b may be defined by signal courses, which may be recognized at each period of the body-surface signal b and thus being representative for the start 48 of the open-state 30 and the end 52 of the open-state 30, respectively.

In an example, known signal detection steps may be performed in order to identify the start-open signal course and/or the end-open signal course at the body-surface signal b. The detection may be the basis for recognizing the start 48 of the open-state 30 of the aortic valve and/or the end 52 of the open-state 30 of the aortic valve, respectively.

In an example, at least two characteristic points q, r of the body-surface signal b following each other indicating the start of a systolic phase of the heart characterizes the start-open signal course.

In a further example, at least two characteristic points t, u of the body-surface signal b following each indicating the end of the systolic phase of the heart characterize the end-open signal course.

As a result, known detection techniques may be used for detecting the characteristic points q, r, s, t, u for each period of the heartbeat. On the basis of the detected characteristic points q, r, s, t, u the start 48 of the open-state 30 of the aortic valve and/or the end 52 of the open-state 30 of the aortic valve may be determined.

As a further result, robust method steps can be used to determine the open-state 30 of the aortic valve, since the determination of the open-state 30 may be based on signals and pre-processed results, which can be provided with known detection techniques. Thus, the determination of the open-state 30 of the aortic valve may also be robust.

According to a further example, the processing unit 14 is configured to determine a closed-state 56 of the aortic valve on the basis of the body-surface signal b, wherein the processing unit 14 is configured to calculate, on the basis of the determined closed-state 56 of the aortic valve, a further display signal component (hereinafter also "third display component") for signaling the aortic valve as closed during the closed-state 56 of the aortic valve.

As explained above, the processing unit 14 is configured to provide a display signal d comprising the display signal components. Thus, the display signal is based on all display signal components, also on the third display signal component.

As a result, the display image may represent the closed-state 56 by the notation 29 to illustrate the aortic valve as closed during the closed-state of the aortic valve. A physician can directly see at the display image 22, whether the aortic valve is opened or closed. During the closed-state 56 of the aortic valve, an advancing of the catheter 44 may be stopped, at least in case the catheter 44 is positioned in front of the aortic valve.

It is understood that, without repeating here all the examples, features and explanations provided with reference to the open-state 30 of the aortic valve, the determination of the closed-state 56 of the aortic valve on the basis of the body-surface signal b may be performed analogous to the determination of the open-state 30 of the aortic valve on the basis of the body-surface signal b.

According to a further example, the processing unit 14 is configured to recognize a start of the closed state 56 of the aortic valve based on a predefined start-close signal course of the body-surface signal b, wherein the processing unit 14 is configured to recognize an end of the closed-state 56 of the aortic valve based on a predefined end-close signal course of the body-surface signal b.

In an example, at least two characteristic points t, u of the body-surface signal b following each other indicating a start of a diastolic phase of the heart characterize the start-close signal course.

In an example, at least two characteristic points p, q of the body-surface signal b following each other indicating an end of a diastolic phase of the heart characterize the end-close signal course.

In an example, the characteristic points t, u, p, q indicate the diastolic phase of the heart. Accordingly, the characteristic points t, u may indicate a start of the diastolic phase and/or the start 58 of the closed-state 56 of the aortic valve. The characteristic points p, q may indicate an end of the diastolic phase and/or the end 60 of the closed-state 56 of the aortic valve.

According to a further example, the processing unit 14 is configured to calculate, on the basis of the ECG-signal, a fourth display signal component for displaying an ECG-signal image 62.

Examples of the ECG-image 62 as an overlay are shown in the display image 22, as exemplarily shown in FIG. 5 and FIG. 6

It is understood that, without repeating here the effect of a further display signal component, the display signal 22 may comprise the ECG image 62. In an example, the display image 22 comprises an ECG-signal image 62 in overlay and/or adjacent to the aortic valve image 20.

In a further example, the ECG-signal image 62 is at least partly transparent.

In a further example, the ECG-signal may be an ECG live signal.

Consequently, a physician may receive from the display image 22 the aortic valve image 20, the ECG-image 62 and the notation 29 indicating whether the aortic valve is at its open-state 30 or closed state 56. The notation 29 may also comprise a further state, namely an intermediate-state of the aortic valve, wherein the intermediate-state may be between the open-state 30 and the closed-state 56, and/or vice versa.

As an effect, the display image 22 may provide a compact overview about relevant information of the aortic valve, especially in case a catheter 44 is supposed to be passed through the aortic valve.

According to a further example, the processing unit 14 is configured to calculate the second display component, such that the open-state 30 of the aortic valve is marked at the ECG-signal image 62 between the start 48 of the open-state 30 of the aortic valve and the end 52 of the open-state 30 of the aortic valve.

In an example, a marker 64 having a rectangular form may be used to mark the open-state 30 of the aortic valve at the ECG-signal image 62.

In an example, a further marker 66 having a rectangular form may be used to mark the closed-state 56 of the aortic valve at the ECG-signal image 62, in particular between the start 58 of the closed-state 56 of the aortic valve and the end 60 of the closed-state 56 of the aortic valve.

In an example, the marker 64, 66 may be at least partly transparent and/or may be arranged in overlay to the ECG-signal image 62.

According to a further example, the processing unit 14 is configured to calculate the second display component, such that at least a part of the aortic valve image 20 is highlighted with a first color between the start 48 of the open-state 30 of the aortic valve and the end 52 of the open-state 30 of the aortic valve.

According to a further example, the processing unit 14 is configured to calculate the third display image component, such that at least a part of the aortic valve image 20 is highlighted with a second color between the start 58 of the closed-state 56 of the aortic valve and the end 60 of the closed-state 56 of the aortic valve.

In an example, the first color is different to the second color.

In an example, the first color is green and the second color is red.

In an example, the highlightings are each at least partly transparent.

According to a further example, the processing unit 14 is configured to recognize, based on the image-data signal g, a tip-position of a tip 68 of a catheter 44 in the aortic valve image 20 and/or the display image 22, wherein the processing unit 14 is configured to recognize, based on the image-data signal g, a valve-position of the aortic valve in the aortic valve image 20 and/or the display image 22, and wherein the processing unit 14 is configured to calculate a catheter-distance between the tip-position and the valve-position, and wherein the processing unit 14 is configured to enable the second and/or the third signal component to be a part of the display signal d, in case the catheter-distance is smaller than a predefined minimum-distance, and disabling the second and/or third signal component to be a part of the display signal otherwise.

As an effect, the display image 22 may comprise the information about a state of the aortic valve, in case catheter 44 is close to the aortic valve. Thus, the information about the state of the aortic valve is just displayed, in case the information is needed. Consequently, information provided at a respective display can be reduced. This may increase the concentration of a physician when using the apparatus 10 and/or the system 24.

Figure 7:
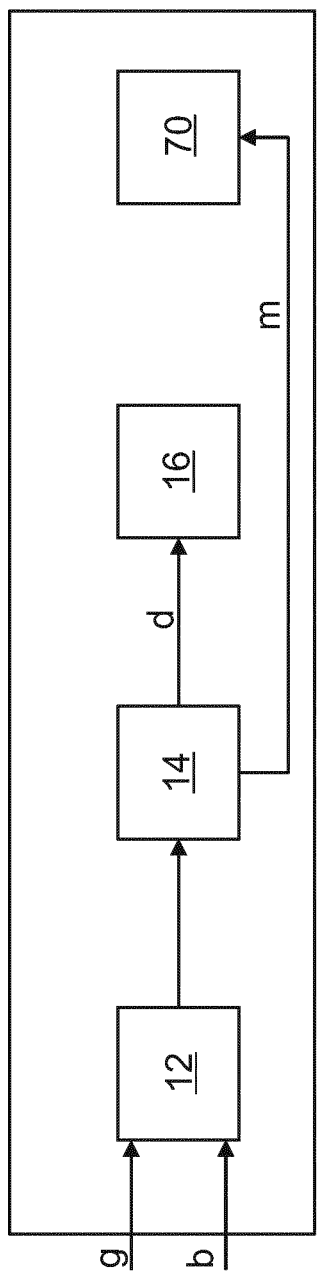
FIG. 7 schematically illustrates a further example of the apparatus.

FIG. 7 exemplarily shows another example of the apparatus 10.

According to a further example, the apparatus 10 may comprise an acoustic output unit 70, wherein the processing unit 14 is configured to calculate, on the basis of the determined open-state 30 of the aortic valve, an acoustic signal m for signaling the aortic valve as open during the open-state 30 of the aortic valve, and wherein the acoustic output unit 70 is configured to acoustically indicate the open-state of the aortic valve on the basis of the acoustic signal m.

As an effect, a physician using the apparatus 10 may acoustically hear, when the aortic valve is at its open-state 30 and thus recognizes the acoustic signal m as a good time for advancing the catheter 44.

As a further effect, a user, in particular the physician may not need to look at the display unit 16 in order to receive the information about the state of the aortic valve, in particular about the open-state 30 of the aortic valve. Consequently, the physician may concentrate on other aspects for placing the catheter 44 at the desired position.

Figure 8:
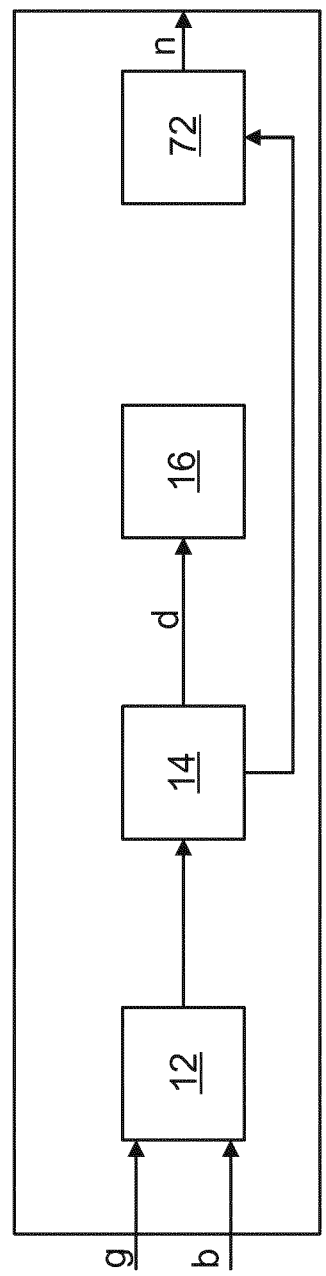
FIG. 8 schematically illustrates a further example of the apparatus.

FIG. 8 exemplarily shows another example of the apparatus 10.

According to a further example, the apparatus 10 comprises an output unit 72, wherein the processing unit 14 is configured to calculate, on the basis of the determined open-state 30 of the aortic valve, an output signal n for signaling the aortic valve as open during the open-state 30 of the aortic valve and wherein the output unit 72 is configured to provide the output signal n for further purposes.

As an effect, the output signal n may be provided to a further unit of the apparatus or to a further device. At the further unit or the further device, the output signal n may be provided to the attention of the user, in particular to a physician. This may be done optically, acoustically and/or haptically.

Figure 9:
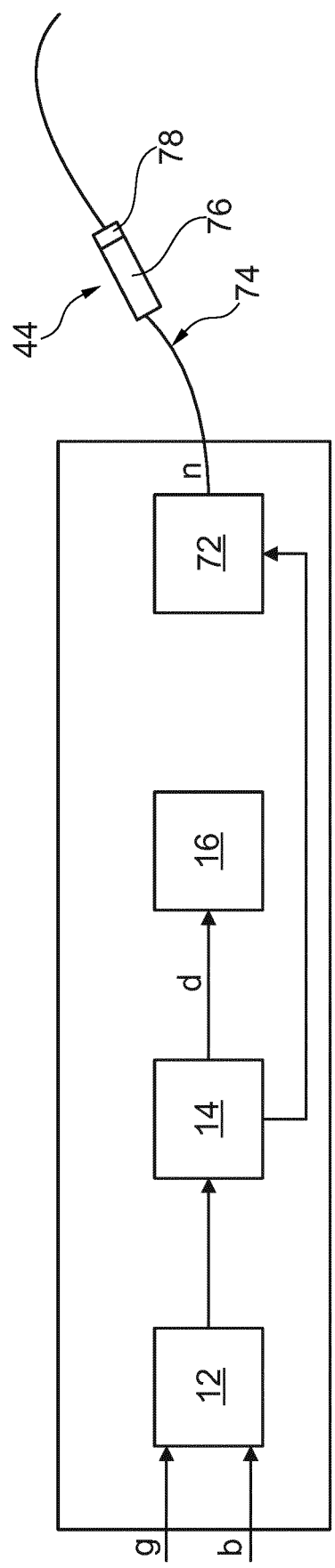
FIG. 9 schematically illustrates a further example of the apparatus.

FIG. 9 exemplarily shows another example of the apparatus 10.

According to a further example, the apparatus 10 comprises a catheter 44 and a signal connection 74, wherein the signal connection 74 connects the output unit 70 of the apparatus 10 and the catheter 44, wherein the catheter 44 comprises a handle 76 to operate the catheter 44, and wherein the catheter 44 comprises at or next to the handle 76 a haptic unit 78, for instance comprising a vibration element, configured to haptically indicate the open-state 30 of the aortic valve on the basis of the output signal.

As an effect, the user of the apparatus 10 handling the catheter 44 may haptically receive the information about the open-state 30 of the aortic valve. Thus, the physician may not need to look at a display unit 16 of the apparatus 10 and thus being able to concentrate on other issues while advancing the guide wire and/or the catheter 44 through the aortic valve.

It is understood that, without repeating here all the examples and explanations provided with reference to the apparatus and/or system of the invention, the method 80 of the invention may be configured to carry out functional features thereof. Thus, all of the above examples and explanations, although firstly provided with reference to the apparatus, may also to be intended as being implemented by the method 80 of the invention. This can be achieved, for example, by means of suitable software.

Figure 10:
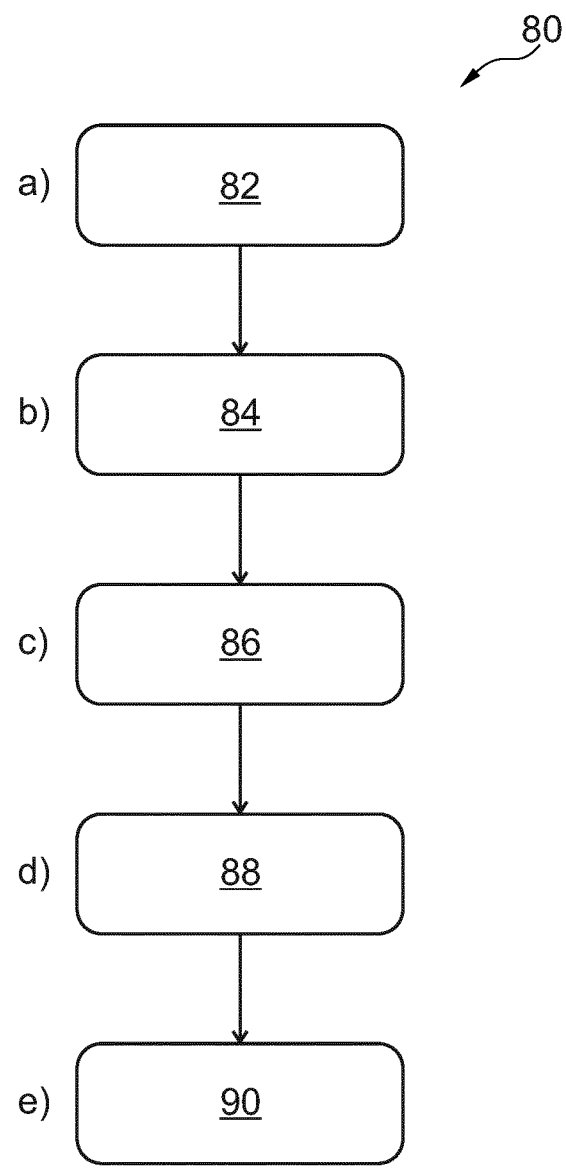
FIG. 10 schematically shows an example of a method according to the present invention.

According to a third aspect of the invention, as exemplarily shown in FIG. 10, a method 80 for signaling a state of an aortic valve is provided, comprising the following:

In a first receiving step 82, also referred to as step a), an image-data signal g indicating an aortic valve image 20 of the heart is received.

In a second receiving step 84, also referred to as step b) a time variant, body-surface signal b indicating a beat of the heart is received.

In a determining step 86, also referred to as step c) an open-state 30 of the aortic valve on the basis of the body-surface signal b is determined.

In an illustrating step 88, also referred to as step d) the aortic valve image 20 of the aortic valve is illustrated on the basis of the image-data signal g.

In a signaling step 90, also referred to as step e) the aortic valve is signaled as open during the open-state 30 of the aortic valve and simultaneously to the illustration of the aortic valve image 20.

In an example, the step c) of the method 80 comprises the sub-step c1): recognizing a start 48 of the open-state 30 of the aortic valve based on a predefined start-open signal course 50 of the body-surface signal b; and the sub-step c2): recognizing an end 52 of the open-state 30 of the aortic valve based on a predefined end-open signal course 54 of the body-surface signal b.

In a further example, the step c) of the method 80 comprises the sub-step c3): determining a closed-state 56 of the aortic valve on the basis of the body-surface signal b; and the sub-step c4): calculating, on the basis of the determined closed-state 56 of the aortic valve, a third display signal component for signaling the aortic valve as closed during the closed-state 56 of the aortic valve.

In a further example, the step c) of the method 80 comprises the sub-step c5): recognizing a start 58 of the closed-state 56 of the aortic valve based on a predefined start-close signal course of the body-surface signal; and the sub-step c6): recognizing an end 60 of the closed-state 56 of the aortic valve based on a predefined end-close signal course of the body-surface signal b.

In an example, the step e) of the method 80 comprises the sub-step e1): illustrating the ECG signal image simultaneously to the illustration of the aortic valve image 20.

In an example, the step e) of the method 80 comprises the sub-step e2): marking the open-state 30 of the aortic valve at the ECG signal image 62 between the start 48 of the open-state 30 of the aortic valve and the end 52 of the open-state 30 of the aortic valve. In an example, the step e) of the method 80 comprises the sub-step e3): highlighting at least a part the aortic valve image with a first color between the start 48 of the open-state 30 of the aortic valve and the end 52 of the open-state 30 of the aortic valve.

In an example, the step c) of the method 80 comprises the sub-step c7): recognizing, based on the image-data signal g, a tip-position of a tip 68 of a catheter 44 in the aortic valve image 20; and the sub-step c8): recognizing, based on the image-data signal g, a valve-position of the aortic valve in the aortic valve image 20; and the sub-step c9): calculating a catheter-distance between the tip-position and the valve-position.

In an example, the step e) of the method 80 comprises the sub-step e4): enabling during the open-state 30 to signal the aortic valve as open and/or to mark the open-state 30 of the aortic valve and/or to highlight at least a part the aortic valve image with a first color; and disabling otherwise to signal the aortic valve as open and/or to mark the open-state 30 of the aortic valve and/or to highlight at least a part the aortic valve image with a first color.

In an example, the method comprises the step f): indicating the open-state 30 and/or the closed-state 56 of the aortic valve acoustically and/or haptically.

According to a fourth aspect of the present invention, a computer program element is provided, which, when being executed by a processing unit, is adapted to carry out the method described above.

According to a fifth aspect of the present invention, a computer-readable medium having stored thereon a program element is provided, which, when being executed by a processing unit, is adapted to carry out the method described above.

It has to be noted that embodiments of the invention are described with reference to different subject matters. In particular, some embodiments are described with reference to an insert whereas other embodiments are described with reference to the apparatus. However, a person skilled in the art will gather from the above that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single interface or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for supporting an aortic valve intervention procedure, comprising:
 a processor configured to:
  receive, during the aortic valve intervention procedure, i) an image-data signal representing an X-ray image of an aortic valve of a heart and an interventional device configured to pass through the aortic valve, and ii) a time variant, body-surface signal indicating a beat of the heart;
  determine a state of the aortic valve on the basis of a predefined signal course of the body-surface signal;
  generate a display signal component for signaling the aortic valve as i) open during a determined open-state of the aortic valve, or ii) as closed during a determined closed-state of the aortic valve; and
  generate a display signal representing a display image comprising the X-ray image and the display signal component, wherein the display image shows an overlay of (i) a portion of the aortic valve, (ii) a portion of the interventional device, and (iii) a notation indicating whether the aortic valve is in the open-state or the closed-state, wherein the notation is overlaid on the aortic valve and configured to show, on the aortic valve, extent of movement of the aortic valve between the open-state and the closed-state; and
 a display configured to display the display image.

2. The apparatus according to claim 1, wherein the body-surface signal is a blood pressure signal.

3. The apparatus according to claim 1, wherein the body-surface signal is an electrocardiography (ECG) signal indicating an electric activity of the heart.

4. The apparatus according to claim 3, wherein the processor is further configured to calculate, on the basis of the ECG signal, a fourth display signal component for displaying an ECG signal image.

5. The apparatus according to claim 4, wherein the processor is further configured to calculate the display component, such that the open-state of the aortic valve is marked at the ECG signal image between the start of the open-state of the aortic valve and the end of the open-state of the aortic valve.

6. The apparatus according to claim 1, wherein the processor is further configured to calculate i) on the basis of the determined closed-state of the aortic valve, a second display signal component for signaling the aortic valve as closed during the determined closed-state of the aortic valve, or ii) on the basis of the determined open-state of the aortic valve, a third display signal component for signaling the aortic valve as open during the determined open state of the aortic valve.

7. The apparatus according to claim 6, wherein the processor is further configured to recognize a start and an end of the open-state and/or the closed-state of the aortic valve based on a respective predefined start-close signal course and/or predefined end-close signal course of the body-surface signal.

8. The apparatus according to claim 1, wherein the processor is configured to calculate the display signal component, such that at least a part of the aortic valve image is highlighted with a first color between the start of the open-state of the aortic valve and the end of the open-state of the aortic valve.

9. The apparatus according to claim 8, wherein a shape of the highlighted part is indicative of an area covered by a movement of the aortic valve between the open state and the closed state.

10. The apparatus according to claim 9, further comprising a catheter, and wherein the processor is configured to:
recognize a tip-position of a tip of the catheter and a valve-position of the aortic valve in the aortic valve image;
calculate a catheter-distance between the tip-position and the valve-position; and
enable the display signal component and/or a further display signal component to be a part of the display signal, in case the catheter-distance is smaller than a predefined minimum-distance, and disabling the display signal component and/or the further display signal component otherwise.

11. The apparatus according to claim 1, wherein the processor is configured to calculate, on the basis of the determined open-state of the aortic valve, and output an acoustic signal for signaling the aortic valve as open during the open-state of the aortic valve.

12. A system for signaling a state of an aortic valve, comprising:
an apparatus according to claim 1;
an X-ray imaging unit configured to acquire the aortic valve image; and
a body-surface signal sensor configured to provide the body-surface signal.

13. A method for signaling a state of an aortic valve, comprising:
receiving, during an aortic valve intervention procedure, an image-data signal representing an X-ray image of an aortic valve of a heart and an interventional device configured to pass through the aortic valve;
receiving a time variant, body-surface signal indicating a beat of the heart;
determining an open-state of the aortic valve on the basis of the body-surface signal;
generating a display signal component for signaling the aortic valve as open during the determined open state of the aortic valve; and
generating a display signal representing a display image comprising the X-ray image and the display signal component, wherein the display image shows an overlay of (i) a portion of the aortic valve, (ii) a portion of the interventional device, and (iii) a notation indicating whether the aortic valve is in the open-state or the closed-state, wherein the notation is overlaid on the aortic valve and configured to show, on the aortic valve, extent of movement of the aortic valve between the open-state and the closed-state.

14. A non-transitory computer-readable storage medium having stored a computer program comprising instructions, the instructions, when executed by a processor, cause the processor to:
receive, during an aortic valve intervention procedure, an image-data signal representing an X-ray image of an aortic valve of a heart and an interventional device configured to pass through the aortic valve;
receive a time variant, body-surface signal indicating a beat of the heart;
determine an open-state of the aortic valve on the basis of the body-surface signal;
generate a display signal component for signaling the aortic valve as open during the determined open state of the aortic valve; and
generate a display signal representing a display image comprising the X-ray image and the display signal component, wherein the display image shows an overlay of (i) a portion of the aortic valve, (ii) a portion of the interventional device, and (iii) a notation indicating whether the aortic valve is in the open-state or the closed-state, wherein the notation is overlaid on the aortic valve and configured to show, on the aortic valve, extent of movement of the aortic valve between the open-state and the closed-state.

* * * * *